(12) United States Patent
Lary et al.

(10) Patent No.: US 7,985,200 B2
(45) Date of Patent: Jul. 26, 2011

(54) APPARATUS FOR DELIVERING AN INTRAVASCULAR DRUG

(75) Inventors: Banning G. Lary, Miami, FL (US); Leonard Pinchuk, Miami, FL (US); Saul Gottlieb, Miramar, FL (US); Charles R. Slater, Fort Lauderdale, FL (US)

(73) Assignee: Lary Research & Development, LLC, Miami, FL (US)

( * ) Notice: Subject to any disclaimer, the term of this patent is extended or adjusted under 35 U.S.C. 154(b) by 1484 days.

(21) Appl. No.: 11/381,372

(22) Filed: May 3, 2006

(65) Prior Publication Data
US 2006/0189930 A1    Aug. 24, 2006

Related U.S. Application Data

(62) Division of application No. 09/898,867, filed on Jul. 3, 2001, now Pat. No. 7,077,836.

(51) Int. Cl.
*A61M 29/00* (2006.01)
(52) U.S. Cl. .................................... 604/101.01
(58) Field of Classification Search ............... 604/96.01, 604/101.01, 104–109; 606/191–194
See application file for complete search history.

(56) References Cited

U.S. PATENT DOCUMENTS

| | | | |
|---|---|---|---|
| 3,625,793 A | 12/1971 | Sheridan et al. | |
| 4,755,172 A * | 7/1988 | Baldwin | 604/131 |
| 4,867,742 A * | 9/1989 | Calderon | 604/28 |
| 4,983,166 A | 1/1991 | Yamawaki | |
| 5,022,399 A | 6/1991 | Biegeleisen | |
| 5,087,244 A | 2/1992 | Wolinsky | |
| 5,109,830 A * | 5/1992 | Cho | 600/108 |
| 5,217,474 A | 6/1993 | Zacca et al. | |
| 5,306,250 A * | 4/1994 | March et al. | 604/104 |
| 5,336,178 A | 8/1994 | Kaplan et al. | |
| 5,338,302 A | 8/1994 | Hasson | |
| 5,536,250 A | 7/1996 | Klein et al. | |

(Continued)

FOREIGN PATENT DOCUMENTS
WO    WO 2004/058337    7/2004

OTHER PUBLICATIONS

Article entitled "Varicose Veins and Intracutaneous Telangiectasia: Combined treatment in 1,500 cases" by Banning G. Lary, in Southern Medical Journal, vol. 80, Sep. 1987, No. 9, 6 pp. 1105-1110.

(Continued)

*Primary Examiner* — Manuel A Mendez
(74) *Attorney, Agent, or Firm* — Gordon & Jacobson, PC

(57) ABSTRACT

A preferred apparatus for delivering an intravascular drug such as a sclerosing agent (or a microfoam sclerosing agent) to a varicose vein includes a catheter having three concentric tubes. The innermost tube has a guide wire lumen and an inflation lumen. The distal end of the innermost tube has an integral inflatable occlusion balloon in fluid communication with the inflation lumen. The intermediate tube has a lumen through which the innermost tube extends. The distal end of the intermediate tube has a self-expanding balloon with a plurality of fluid pores in fluid communication with the intermediate tube lumen. The outer tube has a lumen through which the intermediate tube extends. Sclerosing agent is dispensed through the intermediate tube to pores located at the distal end of the intermediate tube or in the self-expanding balloon. Veins are sclerosed as the self-expanding balloon is pulled through and ultimately out of the vein.

31 Claims, 7 Drawing Sheets

U.S. PATENT DOCUMENTS

| | | | |
|---|---|---|---|
| 5,562,614 A | 10/1996 | O'Donnell | |
| 5,599,306 A | 2/1997 | Klein et al. | |
| 5,609,598 A | 3/1997 | Laufer et al. | |
| 5,611,775 A | 3/1997 | Machold et al. | |
| 5,637,086 A | 6/1997 | Ferguson et al. | |
| 5,676,962 A | 10/1997 | Cabrera Garrido et al. | |
| 5,695,495 A | 12/1997 | Ellman et al. | |
| 5,709,653 A | 1/1998 | Leone | |
| 5,713,863 A | 2/1998 | Vigil et al. | |
| 5,730,136 A | 3/1998 | Laufer et al. | |
| 5,810,847 A | 9/1998 | Laufer et al. | |
| 5,833,650 A | 11/1998 | Imran | |
| 5,868,708 A * | 2/1999 | Hart et al. | 604/104 |
| 5,902,266 A | 5/1999 | Leone et al. | |
| 5,921,954 A | 7/1999 | Mohr, Jr. et al. | |
| 5,947,985 A * | 9/1999 | Imran | 606/159 |
| 6,014,589 A | 1/2000 | Farley et al. | |
| 6,033,397 A | 3/2000 | Laufer et al. | |
| 6,033,398 A | 3/2000 | Farley et al. | |
| 6,036,687 A | 3/2000 | Laufer et al. | |
| 6,063,069 A | 5/2000 | Cragg et al. | |
| 6,071,277 A | 6/2000 | Farley et al. | |
| 6,096,021 A | 8/2000 | Helm et al. | |
| 6,096,054 A | 8/2000 | Wyzgala et al. | |
| 6,102,904 A | 8/2000 | Vigil et al. | |
| 6,103,769 A | 8/2000 | Kelm | |
| 6,113,576 A * | 9/2000 | Dance et al. | 604/164.01 |
| 6,135,991 A | 10/2000 | Muni et al. | |
| 6,149,641 A * | 11/2000 | Ungs | 604/501 |
| 6,152,889 A | 11/2000 | Sopp et al. | |
| 6,165,172 A | 12/2000 | Farley et al. | |
| 6,179,832 B1 | 1/2001 | Jones et al. | |
| 6,190,357 B1 | 2/2001 | Ferrari et al. | |
| 6,200,312 B1 | 3/2001 | Zikorus et al. | |
| 6,264,633 B1 | 7/2001 | Knorig | |
| 6,290,689 B1 | 9/2001 | Delaney et al. | |
| 6,398,780 B1 | 6/2002 | Farley et al. | |
| 6,409,716 B1 | 6/2002 | Sahatjian et al. | |
| 6,440,097 B1 | 8/2002 | Kupiecki | |
| 6,485,500 B1 | 11/2002 | Kokish et al. | |
| 6,503,185 B1 | 1/2003 | Waksman et al. | |
| 6,520,975 B2 | 2/2003 | Branco | |
| 6,524,300 B2 | 2/2003 | Meglin | |
| 6,527,759 B1 | 3/2003 | Tachibana et al. | |
| 6,527,761 B1 | 3/2003 | Buch et al. | |
| 6,533,767 B2 | 3/2003 | Johansson et al. | |
| 6,538,026 B1 | 3/2003 | Krall et al. | |
| 6,544,221 B1 | 4/2003 | Kokish et al. | |
| 6,569,146 B1 | 5/2003 | Werner et al. | |
| 6,663,613 B1 * | 12/2003 | Evans et al. | 604/523 |

OTHER PUBLICATIONS

Downloaded from Internet, information in RITA—radiofrequency Instiial Tissue Ablation (medical devices for minimally invasive surgery), 1 page, at www.ritamedical.com/products.html, date: 2011.

Downloaded from the Internet, press releases for Varisolve, the new (2011) microfoam treatment for varicose veins, 13 pages, @ www.btgplc.com/news.

Product Information "Y connectors", DeRoyal, Powell, TN, Revised May 2002, 2 pages.

* cited by examiner

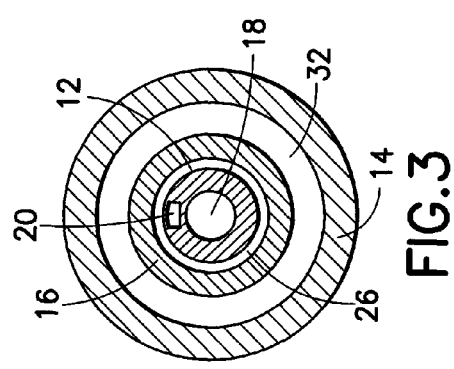
FIG.1
PRIOR ART
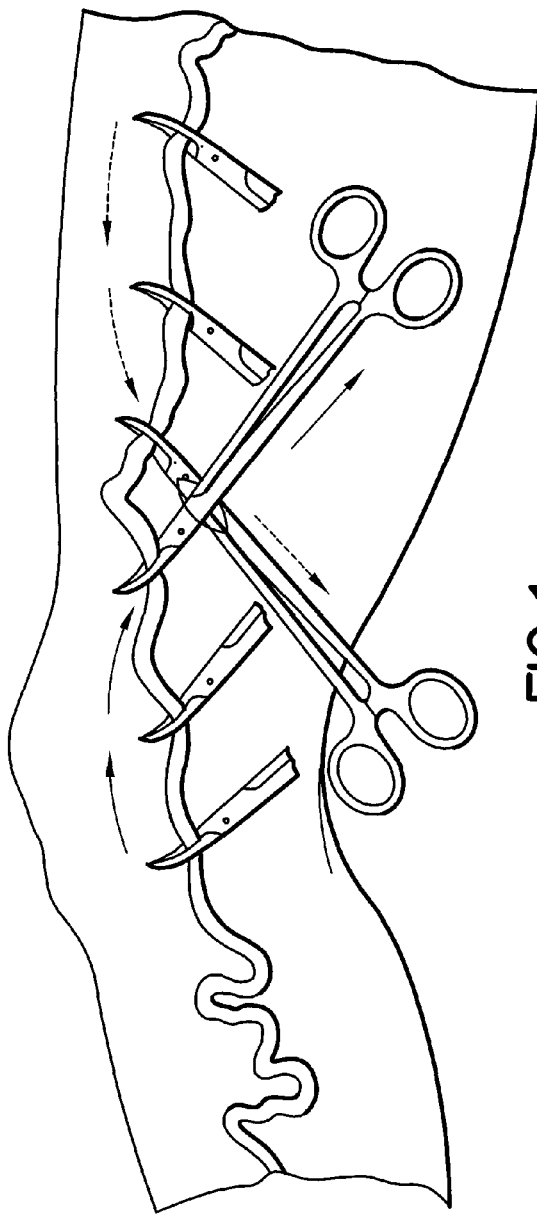
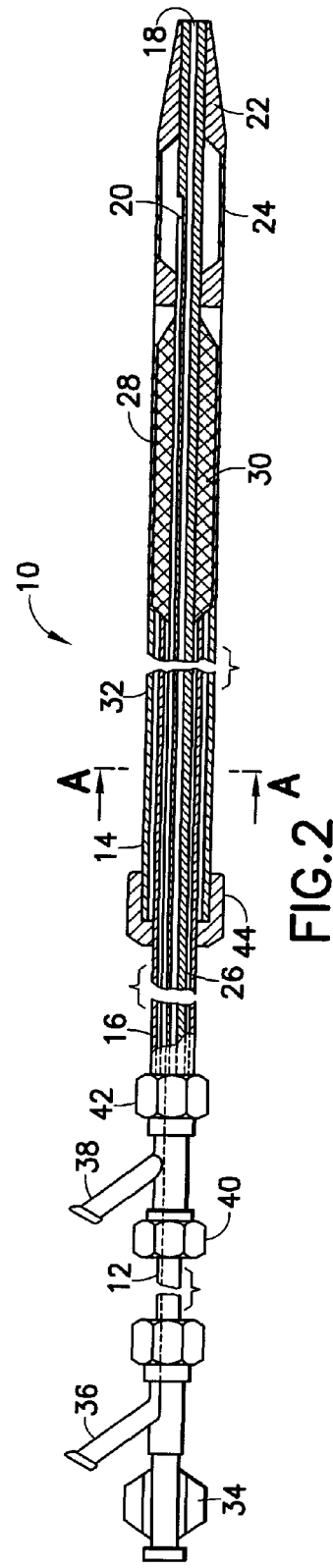
FIG.2
FIG.3

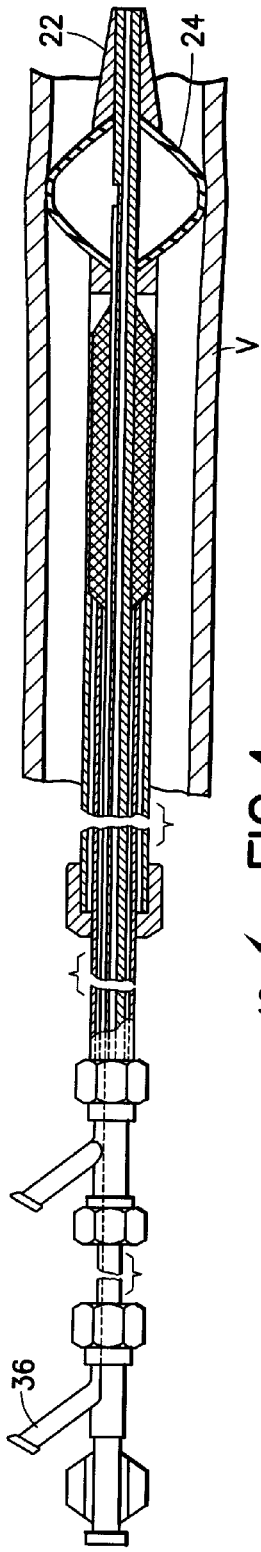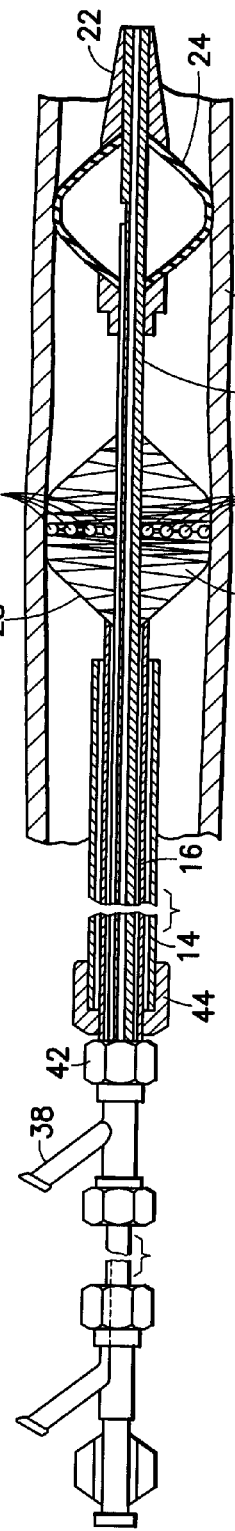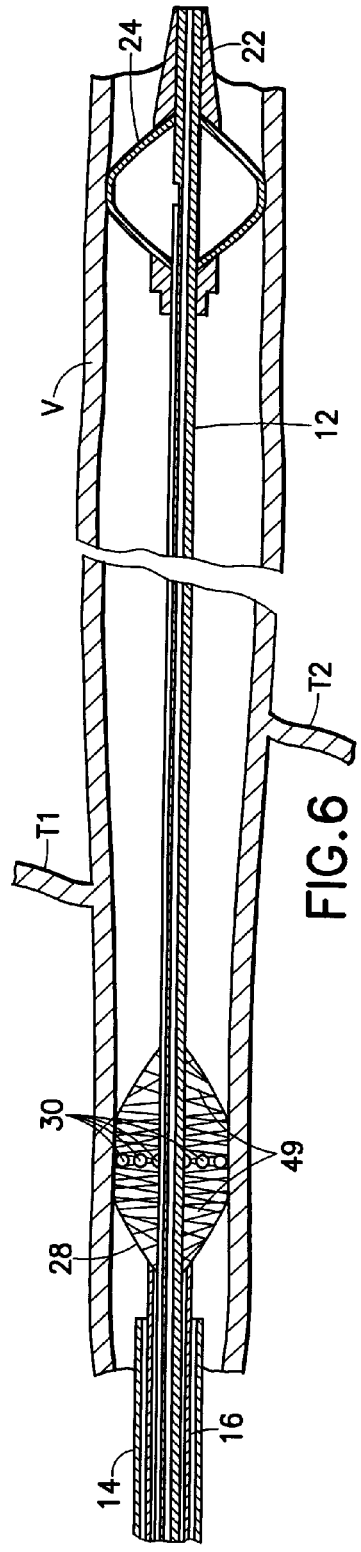

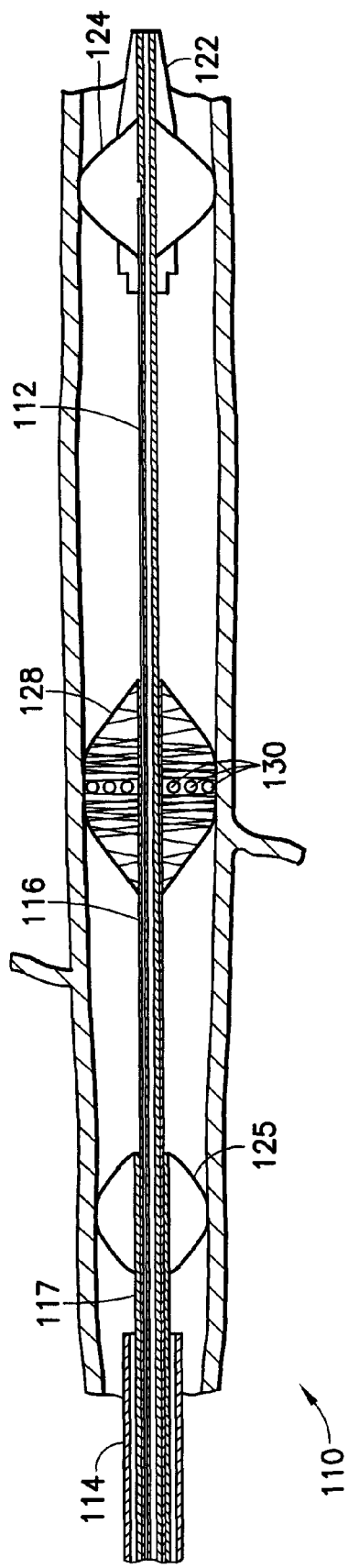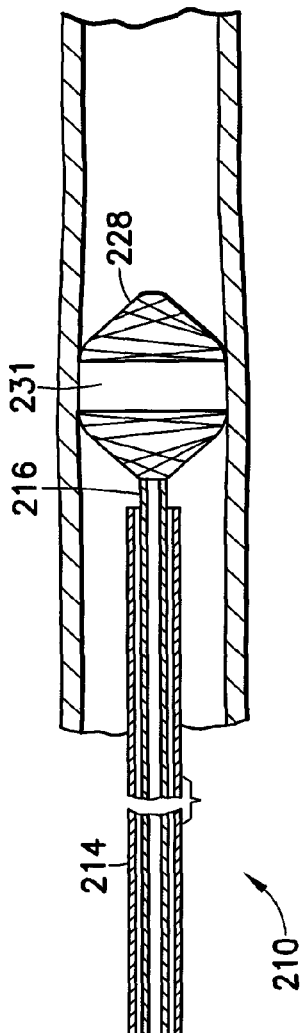
FIG.7
FIG.8

APPARATUS FOR DELIVERING AN INTRAVASCULAR DRUG

This application is a division of serial number 09/898,867, filed Jul. 3, 2001 now U.S. Pat. No. 7,077,836.

BACKGROUND OF THE INVENTION

1. Field of the Invention

The invention relates to the treatment and correction of venous insufficiency or varicose veins. More particularly the invention relates to a minimally invasive procedure using a catheter-based system to sclerose the wall of the vein.

2. State of the Art

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous systems contain numerous one-way valves for directing blood flow back to the heart. Venous valves are usually bicuspid valves, with each cusp forming a sack or reservoir for blood which, under pressure, forces the free surfaces of the cusps together to prevent retrograde flow of the blood and allow antegrade flow to the heart. An incompetent valve is a valve which is unable to close because the cusps do not form a proper seal and retrograde flow of blood cannot be stopped.

Incompetence in the venous system can result from vein dilation. Separation of the cusps of the venous valve at the commissure may occur as a result. Two venous diseases which often involve vein dilation are varicose veins and chronic venous insufficiency.

The varicose vein condition includes dilatation and tortuosity of the superficial veins of the lower limb, resulting in unsightly discoloration, pain and ulceration. Varicose veins often involve incompetence of one or more venous valves, which allow reflux of blood from the deep venous system to the superficial venous system or reflux within the superficial system.

Varicose veins are compatible with long life and rarely cause fatal complications, but the condition significantly decreases the quality of life. Patients complain primarily of leg fatigue, dull, aching pains, ankle swelling, and ulcerations. Occasionally, thrombosis occurs in dilated subcutaneous channels, resulting in local pain, induration, edema, inflammation, and disability. In addition to those problems, the high visibility of the unattractive rope-like swellings and reddish skin blotches causes considerable distress for both men and women. Lastly, varicose eczema, which is a local reddened swollen and itching skin condition can occur and can spread to distant parts of the body (called an "Id reaction").

Phlebosclerosis, the destruction of venous channels by the injection of sclerosing agents, has been used to treat varicose veins since 1853, when Cassaignae and Ebout used ferric chloride. Sodium salicylate, quinine, urea, and sodium chloride have also been used, but the agent more recently favored is sodium tetradecyl sulfate. In order for phlebosclerosis to be effective, it is necessary to evenly dispense the sclerosing agent throughout the wall of the vein without using toxic levels of the sclerosing agent. This is not particularly difficult for the smaller veins. However, it is quite difficult or nearly impossible in larger veins. When a larger vein is injected with a sclerosing agent, the sclerosing agent is quickly diluted by the substantially larger volume of blood which is not present in smaller veins. The result is that the vein is sclerosed (injured) only in the vicinity of the injection. If the procedure is continued, and the injections are far apart, the vein often assumes a configuration resembling sausage links. The problem cannot be cured by injecting a more potent solution of sclerosing agent, because the sclerosing agent may become toxic at such a concentration.

U.S. Pat. No. 5,676,962 discloses an injectable microfoam containing a sclerosing agent. The microfoam is injected into a vein where it expands and, theoretically, achieves the same results as a larger quantity of sclerosing agent without the toxicity. Such a foam is presently manufactured under the trademark Varisolve® by Provensis, Ltd., London, England. Recent clinical trials of the foam indicate a success rate of 81%.

Until recently, the preferred procedure for treating the great saphenous vein was surgical stripping. This highly invasive procedure involves making a 2.5 cm incision in the groin to expose the saphenofemoral junction, where the great saphenous vein and its branches are doubly ligated en masse with a heavy ligature. The distal portion of the vein is exposed through a 1 cm incision anterior to the medial malleolus, and a flat metal or plastic stripper is introduced to exit in the proximal saphenous vein. The leg is held vertically for 30 seconds to empty the venous tree before stripping the vein from the ankle to the groin. If the small saphenous vein is also incompetent, it is stripped at the same time from an incision posterior to the lateral malleolus to the popliteal space. After stripping the veins, the leg is held in the vertical position for three to four minutes to permit vessel ends to retract, constrict, and clot.

After the stripping procedure, collateral veins are removed by the avulsion-extraction technique which is illustrated schematically in prior art FIG. 1. By working through small (5 to 8 mm) transverse incisions, segments of vein 10 to 20 cm long can be removed by dissecting subcutaneously along the vein with a hemostat, and then grasping, avulsing, and removing the vein. With practice, long segments of vein in all quadrants can be removed through these small incisions. No attempt is made to ligate the branches or ends of the veins, since stripping has shown it to be unnecessary. Bleeding is controlled by elevation and pressure for two to four minutes. As many as 40 incisions are made in severe cases, but their small size and transverse direction permit closure with a single suture.

Before closure of the incisions, a rolled towel is rolled repeatedly from the knee to the ankle and from the knee to the groin to express any clots that may have accumulated. The groin incision is approximated with three 5-0 nylon mattress sutures and all other incisions are closed with a single suture.

As can be readily appreciated, the stripping and avulsion-extraction procedures are relatively invasive and require significant anaesthesia. It can therefore be appreciated that it would be desirable to provide an alternative, less invasive procedure which would accomplish the same results as stripping and avulsion-extraction.

Recently, a number of patents have issued disclosing the treatment of varicose veins with RF energy. Illustrative of these recent patents are: U.S. Pat. No. 6,200,312 entitled "Expandable Vein Ligator Catheter Having Multiple Electrode Leads"; U.S. Pat. No. 6,179,832 entitled "Expandable Catheter Having Two Sets of Electrodes"; U.S. Pat. No. 6,165,172 entitled "Expandable Vein Ligator Catheter and Method of Use"; U.S. Pat. No. 6,152,899 entitled "Expandable Catheter Having Improved Electrode Design, and Method for Applying Energy"; U.S. Pat. No. 6,071,277 entitled "Method and Apparatus for Reducing the Size of a Hollow Anatomical Structure"; U.S. Pat. No. 6,036,687 entitled "Method and Apparatus for Treating Venous Insufficiency"; U.S. Pat. No. 6,033,398 entitled "Method and Apparatus for Treating Venous Insufficiency Using Directionally Applied Energy"; U.S. Pat. No. 6,014,589 entitled "Catheter Having Expandable Electrodes and Adjustable Stent"; U.S. Pat. No. 5,810,847 entitled "Method and Apparatus for Minimally Invasive Treatment of Chronic Venous Insufficiency"; U.S. Pat. No. 5,730,136 entitled "Venous Pump Efficiency Test System And Method"; and U.S. Pat. No. 5,609,598 entitled "Method and Apparatus for Minimally Invasive Treatment of Chronic Venous Insufficiency". These patents generally disclose a catheter having an electrode tip which is switchably coupled to a source of RF energy. The catheter is positioned within the vein to be treated, and the electrodes on the catheter are moved toward one side of the vein. RF energy is applied to cause localized heating and corresponding shrinkage of the adjacent venous tissue. After treating one section of the vein, the catheter can be repositioned to place the electrodes to treat different sections of the vein.

Although this procedure has gained acceptance and is less invasive than the stripping and avulsion-extraction procedures, there are several disadvantages to it. In particular, RF treatment is actually quite slow and painful and the patient must be sufficiently anaesthetized along the entire length of the veins to be treated. In addition, repositioning the catheter is time consuming thus requiring anaesthesia for a prolonged period. Moreover, the RF treatment is incomplete, as only a portion of the vein wall is actually treated, i.e. the portion contacting the electrode. The partially treated vein may eventually re-cannularize. Furthermore, tributary veins remain unaffected and must be treated separately.

SUMMARY OF THE INVENTION

It is therefore an object of the invention to provide methods and apparatus for the minimally invasive treatment of varicose veins.

It is also an object of the invention to provide methods and apparatus for the minimally invasive treatment of varicose veins wherein only minimal anaesthesia is required.

It is another object of the invention to provide methods and apparatus for the minimally invasive treatment of varicose veins wherein tributary veins are treated simultaneously with the vein to which they connect.

It is an additional object of the invention to provide methods and apparatus for the minimally invasive treatment of varicose veins and connecting tributaries wherein the entire wall of the vein is evenly sclerosed.

Another object of the invention is to provide methods and apparatus for the minimally invasive treatment of varicose veins which do not utilize high concentration sclerosing agents.

In accord with these objects which will be discussed in detail below, a first embodiment of the present invention includes a catheter having three concentric tubes: an innermost tube, an outer tube, and an intermediate tube. The innermost tube has two lumena: a guide wire lumen and an inflation lumen. The distal end of the innermost tube has an atraumatic tip and an integral inflatable occlusion balloon in fluid communication with the inflation lumen. The intermediate tube has a single lumen through which the innermost tube extends. The distal end of the intermediate tube has a self-expanding balloon with a plurality of fluid pores in fluid communication with the lumen of the intermediate tube. The outer tube has a single lumen through which the intermediate tube extends. The proximal ends of the innermost and intermediate tubes are provided with fluid fittings. The proximal ends of the outer tube and the intermediate tube are provided with sealing fittings.

An exemplary treatment method using the first embodiment of the invention includes elevating the foot above the groin, delivering the catheter via a guide wire into the saphenous vein from the ankle to the groin. The patient is then placed in a Trendelenberg position (the body inclined downward approximately 30 degrees and the leg elevated approximately 60 degrees. The inflatable occlusion balloon is inflated sufficiently to block blood flow, and moving the outer tube relative to the intermediate tube (or vice versa) such that the self-expanding balloon expands and contacts the wall of the vein. With the inflatable occlusion balloon securely in place, the intermediate and outer tubes are pulled away from the inflatable occlusion balloon while sclerosing agent is injected into the lumen of the intermediate tube. The sclerosing agent exits the self-expanding balloon through its pores and directly contacts the wall of the vein. Pressure exerted by the self-expanding balloon both massages the wall of the vein and squeegees sclerosing agent evenly into the vein wall. Collateral tributary veins are injected with sclerosing agent as the self-expanding balloon passes over them. The diameter of the self-expanding balloon becomes progressively smaller as it is moved from the groin area toward the ankle because the diameter of the vein changes accordingly. When the entire vein has been sclerosed, the inflatable occlusion balloon is deflated and the catheter is removed and the incision is sealed. The leg is preferably wrapped with a compression bandage for a few days during which the veins flatten out, thereby removing blood from the vein and allowing the walls of the vein to fuse to itself.

According to the exemplary treatment using the first embodiment of the catheter, only one small incision is made in the ankle and only a small amount of anesthetic is required at the place of the incision. The procedure is relatively painless. Tributary veins are treated simultaneously with the vein into which they feed. The entire wall of the vein is evenly sclerosed. Because blood flow is blocked and sclerosing agent is applied directly to the wall of the vein, a lower concentration of sclerosing agent can be used as it is not diluted by flowing blood. The occlusion balloon also prevents sclerosing agent from exiting the treated vein and entering into another vein.

According to an alternative embodiment, sclerosing agent may be injected through the lumen of the outer tube. In either case, the self-expanding balloon causes the sclerosing agent to be evenly distributed and massaged into the wall of the vein.

A second embodiment of the catheter of the invention has four tubes, two of which are equipped with inflatable occluding balloons. The procedure for using this embodiment involves inflating one balloon upstream and the other downstream and moving the self-expanding balloon between them. The two balloons can be inflated to isolate a tributary for sclerosing.

A third embodiment has only one balloon which massages the wall of the vein as sclerosing agent is injected downstream of the balloon.

A fourth embodiment utilizes a brush having hollow bristles to massage the wall of the vein as sclerosing agent is injected through the bristles.

According to the presently preferred embodiments, a drug dispenser attachment is provided to automatically inject the sclerosing agent as the self-expanding balloon is moved through the vein. The drug dispenser, which may or may not be disposable, attaches to a disposable syringe and includes a rack and pinion gear system for engaging the plunger of the syringe. The gear system is driven by a spool carrying a filament, a ribbon, or a cable. The drug dispenser is attached to the patient's leg with straps and the end of the cable is attached to the intermediate tube of the catheter such that as the self-expanding balloon is moved through the vein, the cable is pulled causing the spool to rotate and the rack and pinion gears to engage the plunger of the syringe and dispense the sclerosing agent. Alternatively, the dispenser may be attached to the catheter and the cable attached to the patient's leg.

In addition to treating varicose veins, the methods and apparatus can be used for the delivery of other intravascular medications such as antiproliferative drugs, for example, Paclitaxel or Rapamycin to coronary arteries and the like, to prevent restenosis of these vessels after stenting. The device can also be used to deliver drugs to other hollow tubes such as the fallopian tubes or to persistent abnormal sinus tracts.

Additional objects and advantages of the invention will become apparent to those skilled in the art upon reference to the detailed description taken in conjunction with the provided figures.

BRIEF DESCRIPTION OF THE DRAWINGS

FIG. 1 is a schematic illustration of a prior art technique for the treatment of varicose veins;

FIG. 2 is a broken side elevation in partial section illustrating a first embodiment of a catheter according to the invention;

FIG. 3 is a sectional view taken along line A-A of FIG. 2;

FIG. 4 is a view similar to FIG. 2 but illustrating the inflatable occlusion balloon inflated inside a vein;

FIG. 5 is a view similar to FIG. 4 but illustrating the self-expanding balloon expanded inside a vein;

FIG. 6 is a view similar to FIG. 5 but illustrating the self-expanding balloon after having traversed a portion of the vein;

FIG. 7 is a view similar to FIG. 6 but illustrating a second embodiment of the catheter of the invention;

FIG. 8 is a view similar to FIG. 7 but illustrating a third embodiment of the invention;

FIG. 8b is an enlarged schematic distal end view of the embodiment of FIG. 8a;

DETAILED DESCRIPTION OF THE PREFERRED EMBODIMENTS

Figure 8A:
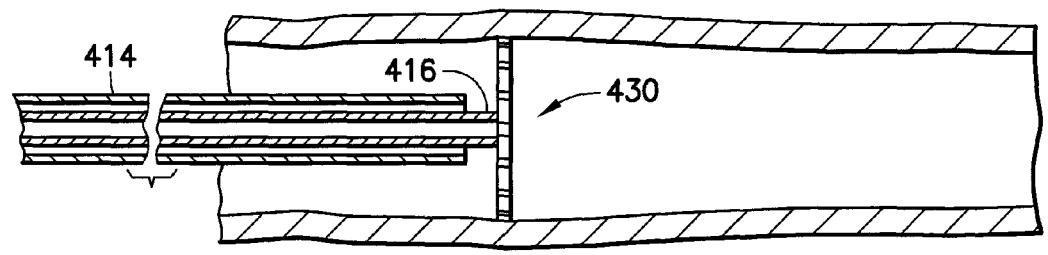
FIG. 8a is a view similar to FIG. 8 but illustrating a fourth embodiment of the invention.

Referring now to FIGS. 2 and 3, a first embodiment of the present invention includes a catheter 10 having three concentric tubes: an innermost tube 12, an outer tube 14, and an intermediate tube 16. The innermost tube 12 has two lumens: a guide wire lumen 18 and an inflation lumen 20. The distal end of the innermost tube includes an atraumatic tip 22 and an integral inflatable occlusion balloon 24 in fluid communication with the inflation lumen 20. The intermediate tube 16 has a single lumen 26 through which the innermost tube extends.

The distal end of the intermediate tube 16 is provided with a self-expanding balloon 28 with a plurality of fluid pores 30 in fluid communication with the lumen 26 of the intermediate tube. The outer tube 14 has a single lumen 32 through which the intermediate tube 16 extends.

The proximal end of the innermost tube 12 has a guide wire hub 34 which provides access to the guide wire lumen 18 and a fluid port 36 in fluid communication with the inflation lumen 20. The proximal end of the intermediate tube 16 is provided with a fluid port 38 in fluid communication with the lumen 26 and two fittings 40, 42. The fitting 40 allows the innermost tube 12 and intermediate tube 16 to be moved relative to each other while maintaining a seal of the annular fluid space between the innermost tube 12 and intermediate tube 16. It will be appreciated that the proximal end of the tube 16 can be reinforced with metal tubing such as thin-walled hypodermic tubing to make it easier to push and provide a more uniform sealing surface. The fitting 42 is either press fit or glued to the proximal end of the intermediate tube 16 or attaches to a luer hub which is press fit or glued to the proximal end of the intermediate tube 16. The proximal end of the outer tube 14 has a fitting 44 that seals the space between the outer tube 14 and the intermediate tube 16 and also releasably locks their relative positions.

An exemplary treatment method using the first embodiment of the invention can be understood with reference to FIGS. 4-6. After anesthetizing the patient's ankle, a guide wire (not shown) is fed into the saphenous vein V from the ankle to the groin of the patient. The guide wire can be fed from a cut-down to the vein at the ankle or by using percutaneous entry techniques well known in the art which generally involves the use of a catheter sheath introducer, and the like. Once the guide wire is in place, the catheter assembly 10 is threaded over the guide wire and follows the guide wire up the leg such that the tip 22 of the occlusion balloon 24 is located in a desired location, e.g., just proximal to the exit of the saphenous vein in the vicinity of the profunda vein. The exact location of the occlusion balloon can be identified by ultrasound, palpation, or by angiography, and the like. The occlusion balloon 24 is then inflated with a gas or fluid through the port 36. $CO_2$ gas is the preferred inflator because it is easy to see with ultrasound and it is safely absorbed into the blood stream should any leakage occur. Once the occlusion balloon 24 is inflated, blood can no longer pass to or from the saphenous vein V via the profunda vein (not shown).

With the inflated occlusion balloon in place, as is shown in FIGS. 4 and 5, the fitting 44 of the outermost tube 14 is loosened and the tube 14 is slid backwards over intermediate tube 16 such that the fitting 44 butts up against connector fitting 42 as shown in FIG. 5. Retracting the outer tube 14 in this manner releases self-expanding balloon 28, which self-expands until it hits the wall of the varicose vein V. The outer abrasive surface of the balloon 28 is now in contact with the wall of the vein.

According to the presently preferred embodiment, the self-expanding balloon 28 is made of a braided mesh, which is braided such that its preferred stable state is fully expanded. The wires of the mesh are of a spring material such as stainless steel, cobalt-chrome-nickel (Elgiloy wire), nitinol or the like. Alternatively, the self-expanding balloon wires may be made of a plastic such as PET, PMMA, polyurethane, nylon or the like. The wires may or may not be heat hardened to impart greater spring-like properties and memory to the mesh. Filling the spaces between the braid wires is a thin membrane 49 made from an elastomeric material such as polyurethane, silicone rubber, polyolefin, polyamide copolymers and the like. The membrane can be formed by dip molding, insert molding or it can be formed separately and glued in place. Those skilled in the art will appreciate that the self-expanding balloon both shortens in length and widens in diameter as it achieves its preferred expanded state. It will be appreciated that the distal end of the balloon 28 is dimensioned such that it can move over the inner tube 12 but still maintain a fluid seal between the balloon 28 and the tube 12. As illustrated in FIGS. 4-6, a plurality of fluid pores 30 in the membrane 49 are located about the circumference of the balloon 28.

When the catheter 10 is in the position shown in FIG. 5, a source of sclerosing agent (or a microfoam containing a sclerosing agent) is coupled to the port 38 and operated to allow sclerosing agent to flow through the annular space between the tubes 12 and 16, into the balloon 28 and out through the pores 30. It will be appreciated that sclerosing agent so dispensed with flow directly into the wall of the vein V. According to the invention, as sclerosing agent is being dispensed, the self-expanding balloon 28 is moved away from the balloon 24 as shown in FIG. 6 by moving the tubes 14 and 16 relative to the tube 12. It will be appreciated that as the balloon 28 is moved along the length of the tapering vein V, the balloon decreases in diameter and lengthens. The sclerosing agent exiting the pores 30 is massaged or "squeegeed" into the wall of the vein V by means of the outward pressure exerted by the balloon 28 against the wall of the vessel V.

FIG. 6 shows the occlusion balloon 24 remaining in place as the self-expanding balloon 28 has traversed along a length of the vessel V. Sclerosing agent is continually injected through the balloon 28 as it is withdrawn. It can also be appreciated that as the balloon 28 passes collateral (tributary) veins such as those identified as T1 and T2, sclerosing agent fills the collateral veins to effectively cause them to sclerose. It will be appreciated that additional sclerosing agent can be injected into the tributary veins by means of a second syringe fluidly coupled to the inlet port 38 by means of a T-connector According to the presently preferred embodiment, the balloon 28 is withdrawn through the entire length of the vein V to be sclerosed. When the entire length is traversed, the occlusion balloon 24 is deflated, the catheter 10 is removed and the puncture site is sealed. Simultaneous with the removal of the occlusion balloon, or just prior to deflation of the balloon, or even during the procedure, the leg of the patient is preferably wrapped with an elastic compression bandage, e.g, an ACE BANDAGE, with other compression objects such as foam, etc. Wrapping the leg in this manner causes the vein to flatten-out, thereby removing blood from the vein and allowing the lumen to fuse to itself in the collapsed embodiment. After a few days of compression the bandages are removed and the vein is no longer medically or cosmetically problematic.

It has been discovered that, due to the "squeegee-like" action of the self-expanding balloon 28, the sclerosing agent need not be dispensed at the outer circumference of the balloon. Thus, the pores 30 of the balloon may be located on the proximal portion of the balloon. Alternatively, the balloon need not have any pores, but pores may be provided at the distal end of the tube 16. As yet another alternative, neither the balloon nor the intermediate tube are provided with pores, but the sclerosing agent is provided via the outer tube 14. In all cases, the sclerosing agent will flow or be forced toward the wall of the vein and be massaged into the vein wall by the balloon 28.

Those skilled in the art will appreciate that if the sclerosing agent is not injected through the balloon 28, the balloon need not be self-expanding. It could be an inflatable balloon which is inflated with a gas or a saline solution from an IV bag, etc.

In this embodiment, the pressure can be adjusted as the balloon traverses the vein and the diameter of the vein changes.

As mentioned above, the catheter of the invention can be used to deliver other types of intravascular medication directly to the wall of a vein. Although the treatment of varicose veins generally involves treating the entire length of the vein, other treatments may require or prefer that only a selected portion of the blood vessel be treated. Accordingly, a second embodiment of the invention is illustrated in FIG. 7 in which two inflatable occlusion balloons are provided to isolate a region of a blood vessel for treatment.

As shown in FIG. 7, the catheter 110 has four tubes: an innermost tube 112, an outer tube 114, and two intermediate tubes 116 and 117. The innermost tube 112 has an inflatable balloon 124 with an atraumatic tip 122 at its distal end. The innermost tube 112 is substantially the same as the tube 12 described above. The outer tube 114 and intermediate tube 116 are also substantially the same as the tubes 14 and 16 described above. The additional tube 117 resides in the annular space between the tubes 114 and 116. It has an inflatable balloon 125 at its distal end and is similar to the tube 112 in that it has two lumen, one of which carries the tube 116 and the other of which is used to inflate the balloon 125. The procedure for using this embodiment involves inflating one balloon upstream and the other downstream and moving the self-expanding balloon between them while injecting an intravascular drug. This allows treatment of a selected portion of a blood vessel without diluting the treatment drug. It will also be appreciated that the catheter 110 can also be used to isolate one or a plurality of tributary veins by inflating the balloons on opposite sides of the tributary or tributaries. Sclerosing agent is then injected between the balloons and forced into the tributary or tributaries, A third embodiment of a catheter 210 according to the invention is shown in FIG. 8. This embodiment includes an outer tube 214 and an inner tube 216. The distal end of the inner tube 216 is provided with a self-expanding balloon 228. According to this embodiment, the balloon 228 is optionally provided with an abrasive surface 231 and/or pores (not shown). When an abrasive surface is provided, the catheter 210 may be used with or without a sclerosing agent. In these instances, treatment may consist of abrading the wall of the blood vessel with the abrasive surface 231 of the balloon 228. In other instances, where pores are provided in the balloon, treatment may consist of abrading the wall of the vain (if the balloon has an abrasive surface) as the sclerosing agent is injected out of the pores. In yet other instances, when no pores are provided in the balloon, treatment may include injecting an intravascular drug through the annular space between the outer tube 214 and the inner tube 216 or through pores (not shown) at the distal end of the inner tube 216. If the balloon 228 is moved against the flow of the drug (from right to left as seen in FIG. 8), the drug will be massaged into the wall of the blood vessel (which is abraded if the balloon has an abrasive surface) by the balloon 228.

Figure 8B:
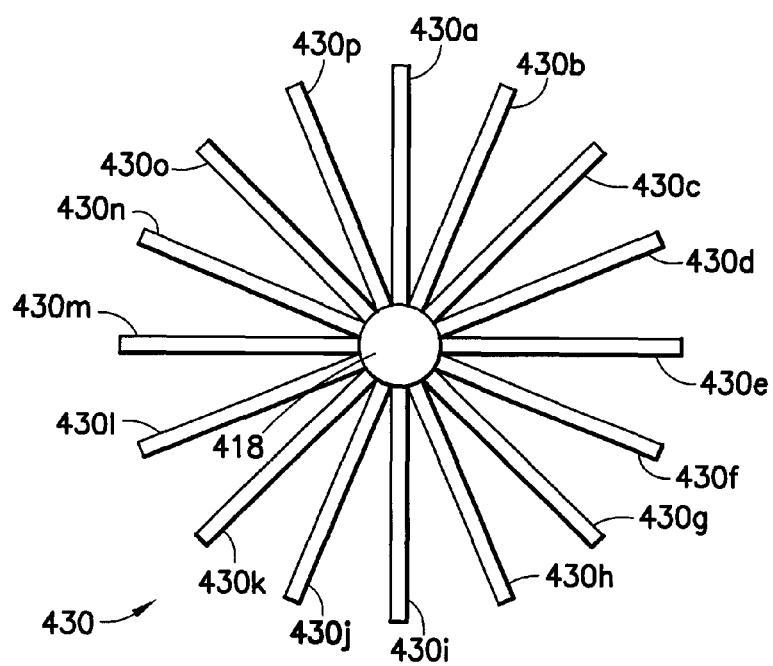

A fourth embodiment of a catheter 410 according to the invention is shown in FIGS. 8a and 8b. This embodiment includes an outer tube 414 and an inner tube 416. The distal end of the inner tube 416 is provided with a brush 430 having a plurality of hollow bristles, e.g. 430a-430p and a plug 418. The hollow bristles are in fluid communication with the inner tube 416 such that a sclerosing agent may be injected through the tube 416 and exit the ends of the bristles. The bristles 430a-420p are preferably made of a resilient material so that they will expand to the position shown in the Figures, i.e., approximately radial to the inner tube, when released from the outer tube. A method for using the fourth embodiment includes moving the outer tube and/or inner tube until the bristles 430a-420p are collapsed inside the outer tube, delivering the two tubes to a procedural site in a blood vessel, moving the outer tube and/or inner tube until the bristles 430a-420p are expanded as shown in the figures, then moving the inner tube relative to the blood vessel while injecting a sclerosing agent through the inner tube and the bristles.

Figure 9:
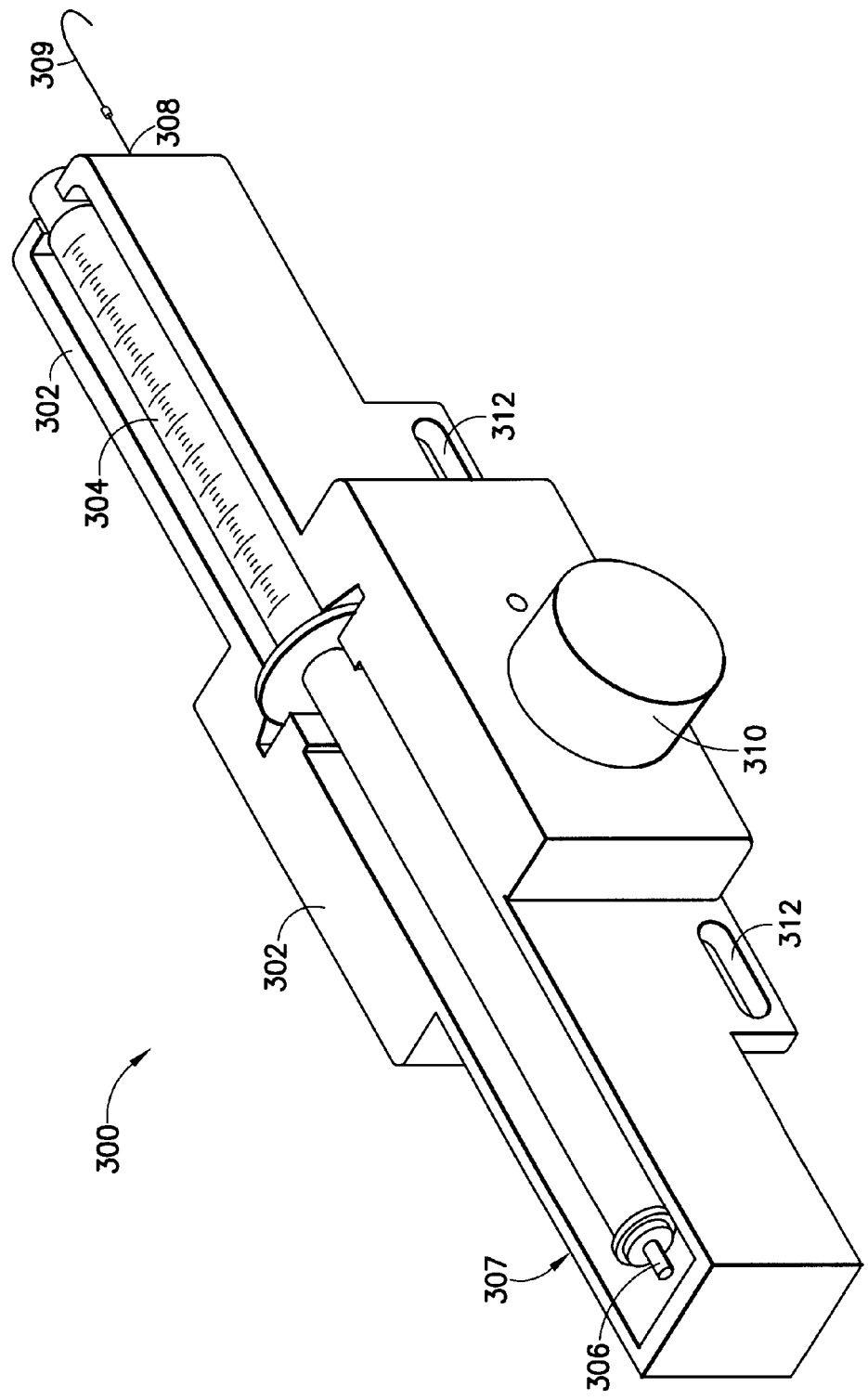
FIG. 9 is a perspective view of a drug dispenser according to the invention.

According to the presently preferred embodiments, a drug dispenser attachment is provided to automatically inject the sclerosing agent as the self-expanding balloon is moved through the vein. FIG. 9 shows a three dimensional view of a drug dispenser 300 with a body 302 defining a channel for receiving a disposable syringe 304, an injector cam 306, a string 308 with a hook 309, a winding clutch 310 (shown in further detail in FIG. 11) and slots 312.

Figure 10:
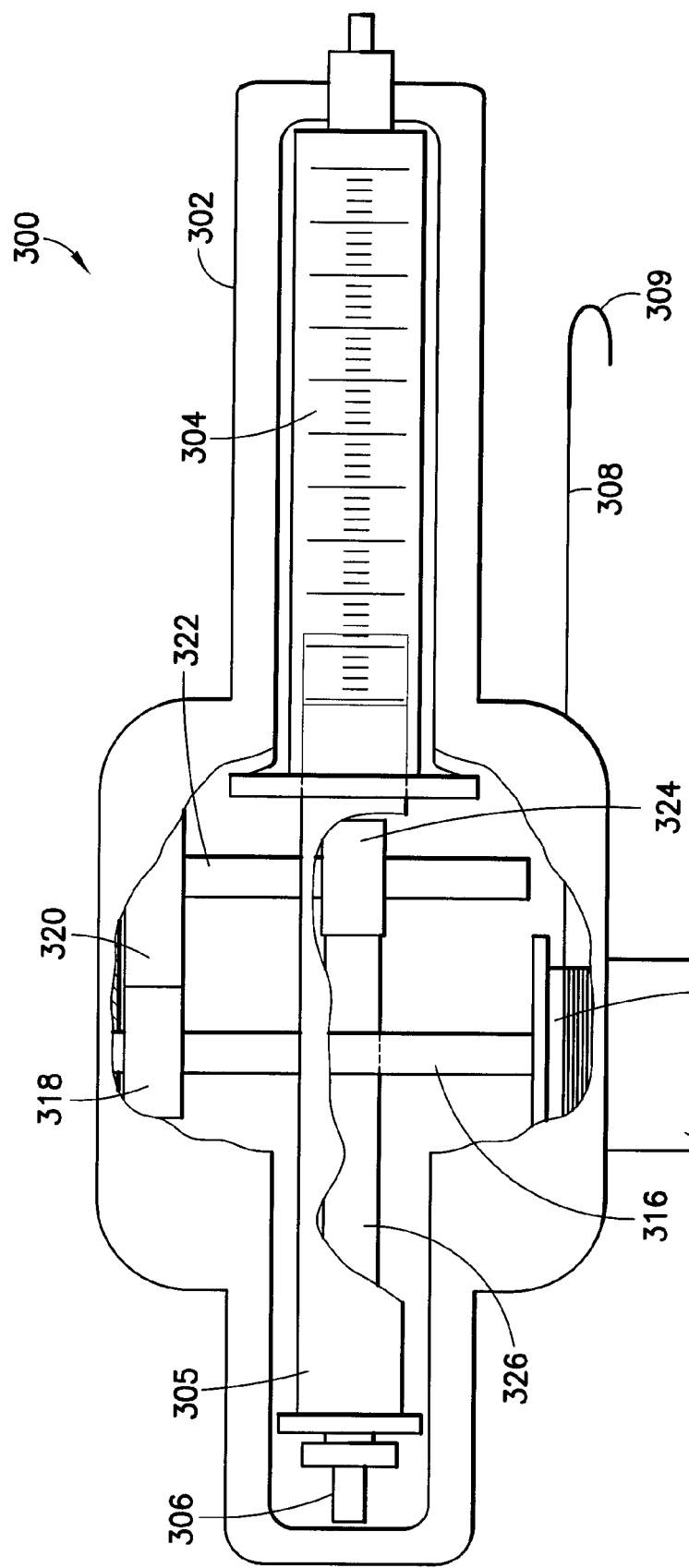
FIG. 10 is a partially cut away top view of the drug dispenser of FIG. 9.

FIG. 10 is a partially cut away top view of the dispenser 300. As shown in FIG. 10, the string 308 with hook 309 is wound on spool 314. The spool 314 is rigidly attached to the winding clutch 310 and clutchingly attached to an axle 316. The axle 316 is rigidly attached to a spur gear 318. The spur gear 318 engages a second spur gear 320, which in turn is rigidly attached to an axle 322 which carries a pinion gear 324. The pinion gear 324 engages a rack 326, which is attached to the injector cam 306. As seen in FIG. 10, the injector cam 306 is aligned with the plunger 305 of the disposable syringe 304.

Figure 11:
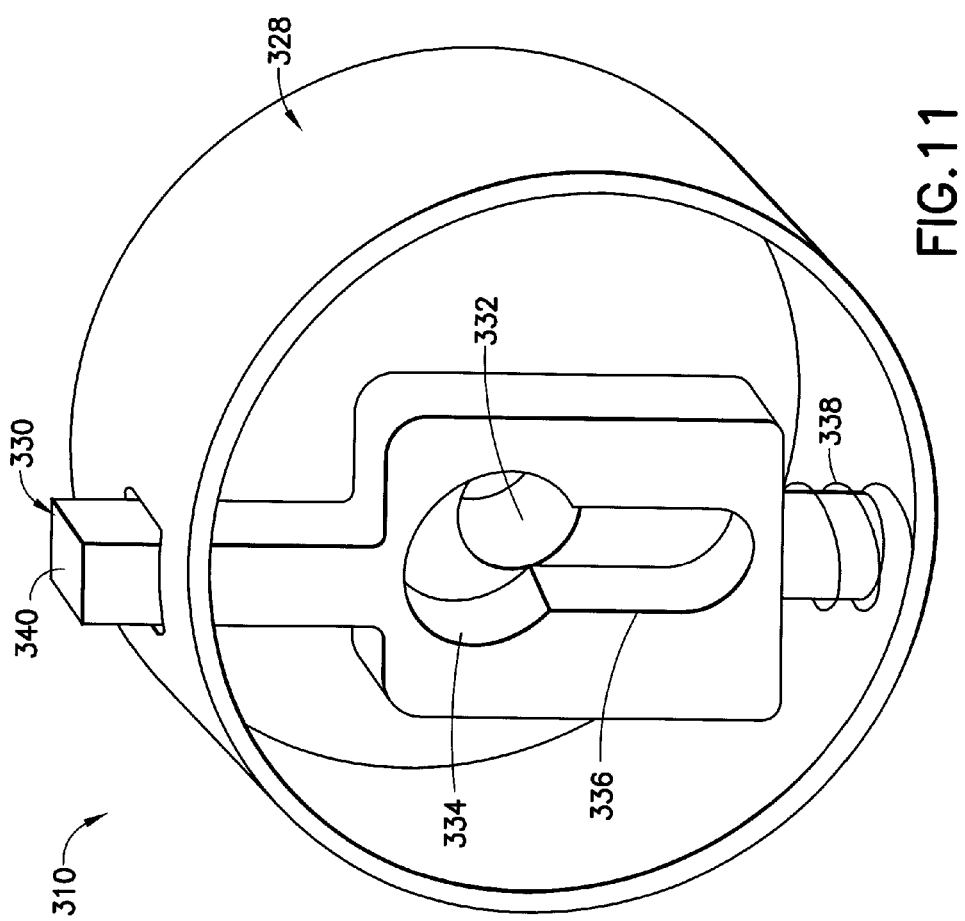
FIG. 11 is an enlarged perspective view of a winding clutch of the drug dispenser.

As seen in FIG. 11, the winding clutch 310 includes a clutch housing 328 and a cam 330. The clutch housing 328 defines a center hole 332 through which the axle (316 in FIG. 10) extends. The cam 330 defines a hole 334 with an adjacent keyway 336. The cam 330 is spring biased by a spring 338 so that the keyway 336 aligns with the hole 332 and engages flats (not shown) which are machined on the axle (316 in FIG. 10). When the cam 330 is pressed at 340, the hole 334 lines up with the hole 332 and the flats on the axle are no longer engaged causing clutch 310 to rotate without engaging the axle and without dispensing sclerosing agent from syringe 304. This feature allows the string 305 to be wound onto the spool 314. It also provides the surgeon with a mechanism to lengthen or shorten the string without dispensing sclerosing agent from the syringe.

The drug dispenser 300 works as follows. The body 302, with the exit of the syringe 304 pointed towards the patient's foot, is fastened to the patient's leg, preferably adjacent the ankle, via straps such as VELCRO straps which are fed through the slots 312. The sclerosing catheter (e.g. 10 in FIG. 2) is maneuvered into the patient's vein from a puncture site in the patient's ankle. The proximal hub 42 (FIG. 2) of the sclerosing catheter is attached to the hook 309 at the end of the string 308. As the sclerosing catheter is pulled out of the vein, tension on string 308 causes pulley 314 to rotate which causes the pinion 324 to rotate (via gears 318 and 320) and rack 326 to move. The cam 306 on the rack 326 presses the plunger 305 causing sclerosing agent to be discharged from syringe 304. Those skilled in the art will appreciate that a fluid conduit may be required to couple the fluid exit of the syringe 304 to the fluid port 38 (FIGS. 2, 4, and 5). It will also be appreciated that the gear ratios of the drug dispenser can be selected such that the appropriate volume of sclerosing agent dispenses as the catheter is pulled out of the leg. The main purpose of the injector is to allow the physician to dispense a continuous amount of sclerosing agent into the patient as a function of the withdrawal of the catheter. It can be appreciated that no sclerosing agent is discharged if the catheter is not pulled and that the flow rate of sclerosing agent tracks the speed at which the catheter is withdrawn. As mentioned above, the drug dispenser can be used in conjunction with one of the catheters to dispense other kinds of intravascular drugs for different procedures.

Those skilled in the art will appreciate that the drug dispenser may be attached to the catheter and the string attached to the patient's leg. Moreover, it will be appreciated that the clutch may be omitted if an adjustable length cable is used. It will also be appreciated that other types of clutches could be used at any of the gears or axles.

There have been described and illustrated herein several embodiments of methods and apparatus for sclerosing the wall of a varicose vein. While particular embodiments of the invention have been described, it is not intended that the invention be limited thereto, as it is intended that the invention be as broad in scope as the art will allow and that the specification be read likewise. For example, the catheter can be provided with an integral guide wire and the catheter and the guide wire can be inserted simultaneously. Also, the dual lumen catheter can be formed by two concentric tubes with the inflation lumen being the annular space between the tubes. It will therefore be appreciated by those skilled in the art that yet other modifications could be made to the provided invention without deviating from its spirit and scope as so claimed.

The invention claimed is:

1. An apparatus for delivering an intravascular drug, said apparatus comprising:
    a) a first catheter tube having a proximal end, a distal end, and a fluid lumen extending from its proximal end to its distal end;
    b) an inflatable balloon coupled to said distal end of said first catheter and in fluid communication with said fluid lumen;
    c) a second catheter tube having a proximal end, a distal end, and a lumen extending from its proximal end to its distal end, said first catheter tube extending through said lumen of said second catheter tube;
    d) a self-expanding balloon coupled to said distal end of said second catheter tube, said first catheter tube extending through said self-expanding balloon; and
    e) a third catheter tube having a proximal end, a distal end, and a lumen extending from its proximal end to its distal end, said second catheter tube extending through said lumen of said third catheter tube, wherein
    at least one of said second catheter tube and said third catheter tube is adapted to receive and deliver the intravascular drug to the location of said self-expanding balloon.

2. An apparatus according to claim 1, wherein:
    said first catheter tube has a guide wire lumen extending from its proximal end to its distal end.

3. An apparatus according to claim 1, wherein:
    said second catheter tube is adapted to receive and deliver the intravascular drug, and
    said self-expanding balloon includes a plurality of fluid pores, said fluid pores being in fluid communication with said lumen of said second catheter tube.

4. An apparatus according to claim 1, wherein:
    said second catheter tube is adapted to receive and deliver the intravascular drug, and
    said distal end of said lumen of said second catheter tube has a plurality of fluid pores.

5. An apparatus according to claim 1, wherein:
    said third catheter tube is adapted to receive and deliver the intravascular drug.

6. An apparatus according to claim 1, wherein:
said third catheter tube has a proximal locking means for locking the location of said second catheter tube relative to said third catheter tube.

7. An apparatus according to claim 1, wherein:
said first catheter tube is adapted to receive the intravascular drug by having a proximal port in fluid communication with said fluid lumen of said first catheter tube.

8. An apparatus according to claim 1, wherein:
said second catheter tube is adapted to receive the intravascular drug by having a proximal port at said proximal end of said second catheter tube in fluid communication with said fluid lumen of said second catheter tube.

9. An apparatus according to claim 1, further comprising:
f) a fourth catheter tube having a proximal end, a distal end, and a lumen extending from its proximal end to its distal end, said third catheter tube extending through said lumen of said fourth catheter tube; and
g) a second inflatable balloon coupled to the distal end of said fourth catheter.

10. An apparatus according to claim 1, further comprising:
f) a drug dispenser having a drug reservoir and a drug outlet, said drug outlet being fluidly coupled to said fluid delivery means, said drug dispenser being adapted to automatically dispense the drug from the reservoir into the fluid delivery means as said second catheter tube is moved through a blood vessel.

11. An apparatus according to claim 10, wherein:
said drug reservoir is a syringe having a plunger, and
said drug dispenser includes means for moving said plunger as said second catheter tube is moved through a blood vessel.

12. An apparatus according to claim 11, wherein:
said means for moving said plunger includes a gear coupled to said plunger, a spool coupled to said gear, and a filament, ribbon, or cable coupled to said spool.

13. An apparatus according to claim 10, wherein:
said drug dispenser includes means for coupling said drug reservoir to a patient's limb.

14. An apparatus according to claim 10, wherein:
said drug dispenser includes means for coupling said drug reservoir to one of said catheter tubes.

15. An apparatus according to claim 1, wherein:
said self-expanding balloon is disposed with said lumen of said third catheter tube in an unexpanded state and self expands into an expanded state when deployed outside said lumen of said third catheter tube.

16. An apparatus for delivering an intravascular drug, said apparatus comprising:
a) a catheter having a proximal end, a distal end, and a lumen extending from its proximal end to its distal end;
b) a drug reservoir having a drug outlet, said drug outlet being fluidly coupled to the proximal end of the lumen of the catheter,
c) dispensing means coupled to said drug reservoir, said dispensing means being adapted to automatically dispense the drug from the reservoir into the lumen of the catheter as the catheter is moved through a blood vessel, wherein said dispensing means includes an actuator that is placed in tension in response to movement of said catheter through the blood vessel, the actuator controlling operation of said dispensing means in response to movement of said catheter through the blood vessel.

17. An apparatus according to claim 16, wherein:
said drug reservoir is a syringe having a plunger, and
said dispensing means includes means for moving said plunger as said catheter is moved through a blood vessel.

18. An apparatus according to claim 17, wherein:
said means for moving said plunger includes a gear coupled to said plunger and a spool coupled to said gear; and
said actuator comprises a filament, pullwire, ribbon, or cable coupled to said spool.

19. An apparatus according to claim 16, further comprising:
d) attachment means for attaching said drug reservoir to a patient's limb.

20. An apparatus according to claim 16, further comprising:
d) attachment means for attaching said drug reservoir to said catheter.

21. An apparatus for delivering an intravascular drug, said apparatus comprising:
a) a first catheter tube having a proximal end, a distal end, and a lumen extending from its proximal end to its distal end;
b) a self-expanding balloon coupled to said distal end of said first catheter tube; and
c) a second catheter tube having a proximal end, a distal end, and a lumen extending from its proximal end to its distal end, said first catheter tube extending through said lumen of said second catheter tube, wherein
at least one of said first catheter tube and said self-expanding balloon includes pores, and said first catheter tube is adapted to receive and deliver the intravascular drug to said pores.

22. An apparatus according to claim 21, wherein:
said self-expanding balloon is comprised of spring wires and a thin membrane coupled to said spring wires.

23. An apparatus according to claim 21, wherein:
said self-expanding balloon includes an abrasive outer surface.

24. An apparatus according to claim 21, wherein:
said self-expanding balloon is made of plastic.

25. An apparatus according to claim 21, wherein:
said self-expanding balloon is disposed with said lumen of said second catheter tube in an unexpanded state and self expands into an expanded state when deployed outside said lumen of said second catheter tube.

26. An intravascular apparatus, comprising:
a) a first catheter tube having a proximal end, a distal end, and a lumen extending from its proximal end to its distal end;
b) a self-expanding balloon coupled to said distal end of said first catheter tube and having an abrasive outer surface; and
c) a second catheter tube having a proximal end, a distal end, and a lumen extending from its proximal end to its distal end, said first catheter tube extending through said lumen of said second catheter tube.

27. An intravascular apparatus according to claim 26, wherein:
at least one of said first catheter tube and said self-expanding balloon includes pores, and said first catheter tube is adapted to receive and deliver an intravascular drug to said pores.

28. An intravascular apparatus according to claim 26, wherein:
said self-expanding balloon is disposed with said lumen of said second catheter tube in an unexpanded state and self expands into an expanded state when deployed outside said lumen of said second catheter tube.

29. A kit for the intravascular treatment of a blood vessel, said kit comprising:

a) a catheter having an expandable balloon at its distal end and a drug delivery lumen; and
b) a drug dispenser having a drug reservoir fluidly coupled to said drug delivery lumen, wherein said drug dispenser includes dispensing means for automatically dispensing a drug from said drug reservoir into said drug delivery lumen in response to movement of said catheter through the blood vessel, wherein said dispensing means includes an actuator that is placed in tension in response to movement of said catheter through the blood vessel, the actuator controlling operation of said dispensing means in response to movement of said catheter through the blood vessel.

30. A kit according to claim 29, wherein:
said drug reservoir includes a syringe having a plunger and said means for automatically dispensing includes means for depressing said plunger.

31. A kit according to claim 30, wherein:
said means for depressing said plunger includes a gear coupled to said plunger and a spool coupled to said gear; and
said actuator comprises a filament, pullwire, ribbon, or cable coupled to said spool.

* * * * *